(12) United States Patent
Blendermann

(10) Patent No.: US 9,636,310 B1
(45) Date of Patent: *May 2, 2017

(54) METHOD FOR INCREASING MUSCLE STRENGTH

(71) Applicant: Edward Ludwig Blendermann, Palm City, FL (US)

(72) Inventor: Edward Ludwig Blendermann, Palm City, FL (US)

(73) Assignee: Edward Ludwig Blendermann, Palm City, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/163,641

(22) Filed: May 24, 2016

Related U.S. Application Data

(63) Continuation of application No. 13/987,482, filed on Jul. 30, 2013, which is a continuation of application No. 10/302,527, filed on Nov. 25, 2002, now Pat. No. 8,617,590, which is a continuation-in-part of application No. 09/243,753, filed on Feb. 3, 1999, now abandoned.

(51) Int. Cl.
| | |
|---|---|
| *A61K 9/20* | (2006.01) |
| *A61F 13/00* | (2006.01) |
| *A61K 9/70* | (2006.01) |
| *A61K 9/00* | (2006.01) |
| *A61K 31/4172* | (2006.01) |
| *A61K 31/185* | (2006.01) |
| *A61K 31/198* | (2006.01) |
| *A61K 31/221* | (2006.01) |
| *A61K 31/197* | (2006.01) |

(52) U.S. Cl.
CPC ............ *A61K 9/7084* (2013.01); *A61K 9/009* (2013.01); *A61K 9/0014* (2013.01); *A61K 31/185* (2013.01); *A61K 31/197* (2013.01); *A61K 31/198* (2013.01); *A61K 31/221* (2013.01); *A61K 31/4172* (2013.01)

(58) Field of Classification Search
CPC .................................. A61K 9/20; A61F 3/00
USPC .................................................. 424/449, 464
See application file for complete search history.

(56) References Cited

U.S. PATENT DOCUMENTS

| | | | |
|---|---|---|---|
| 4,856,651 | A | 8/1989 | Francis |
| 5,005,374 | A | 4/1991 | Spitler |
| 5,131,409 | A | 7/1992 | Lobarev et al. |
| 5,233,981 | A | 8/1993 | Miyashita |
| 5,289,644 | A | 3/1994 | Driskill |
| 6,142,927 | A | 11/2000 | Clark et al. |

(Continued)

FOREIGN PATENT DOCUMENTS

| | | |
|---|---|---|
| CN | 1133744 A | 10/1996 |
| WO | PCT/US2014/000169 | 2/2015 |

OTHER PUBLICATIONS

Carnitine, https://web.archive.org/web/20070927202020/http://en.wikipedia.org/wiki/Carnitine.*

(Continued)

*Primary Examiner* — San-Ming Hui

(57) ABSTRACT

A method of increasing strength using a nutrient holding device (pedal device, hat band, necklace, locket, belt, etc.) which contains at least one nutrient which has the ability to stimulate reflex zones on the skin resulting in improved performance when worn during athletic endeavors (exercise).

26 Claims, 9 Drawing Sheets

(56) References Cited

U.S. PATENT DOCUMENTS

| | | | |
|---|---|---|---|
| 6,148,822 | A | 11/2000 | Cron et al. |
| 6,277,142 | B1 | 8/2001 | Pinter |
| 6,475,514 | B1 | 11/2002 | Blitzer et al. |

OTHER PUBLICATIONS

How to Make Amulets, Charms and Talismans: What They Mean and How to Use Them, Oct. 1994 (Lippman, ISBN 0806515724); pp. 9, 97, 125-127.
Running for Fitness, Oct. 31, 2002 (Owen Barder, ISBN 0713651393).
Decision Denying Institution of Inter Partes Review, Case IPR2016-00131, U.S. Pat. No. 8,617,590 B2; Apr. 26, 2016.
Decision Denying Institution of Inter Partes Review, Case IPR2016-00571, U.S. Pat. No. 8,617,590 B2; Sep. 7, 2016.
SP Systems, The Advantages of Epoxy Resin versus Polyester in Marine Composite Structures, 2005.
Expert Report including Exhibits, C. Norman Shealy, Civil Action No. 2:15-cv-14265-RLR-FJL (Feb. 22, 2107).
Complaint, *Edward L Blendermann* v. *Lifewave Inc*. Civil Action No. 2:15-cv-14265-RLR-FJL (Jul. 29, 2015).
Answer, Defenses and Counterclaims, *Edward L Blendermann* v. *Lifewave Inc*. Civil Action No. 2:15-cv-14265-RLR-FJL (Sep. 28, 2015).
Expert Report including Exhibits, Ilya Skolnikoff, Civil Action No. 2:15-cv-14265-RLR-FJL (Feb. 21, 2107).
Expert Report including Exhibits, Lisa Tully, Civil Action No. 2:15-cv-14265-RLR-FJL (Feb. 22, 2107).

\* cited by examiner

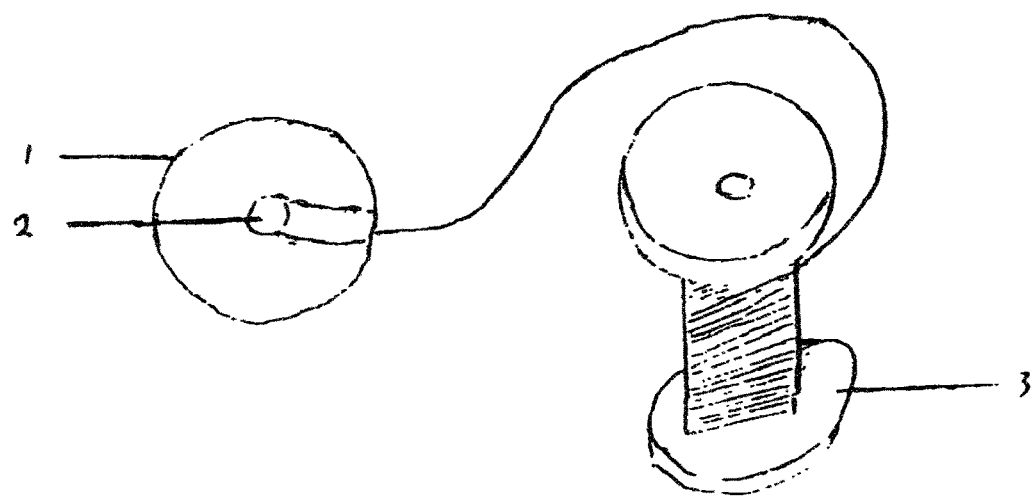
FIG. 5A
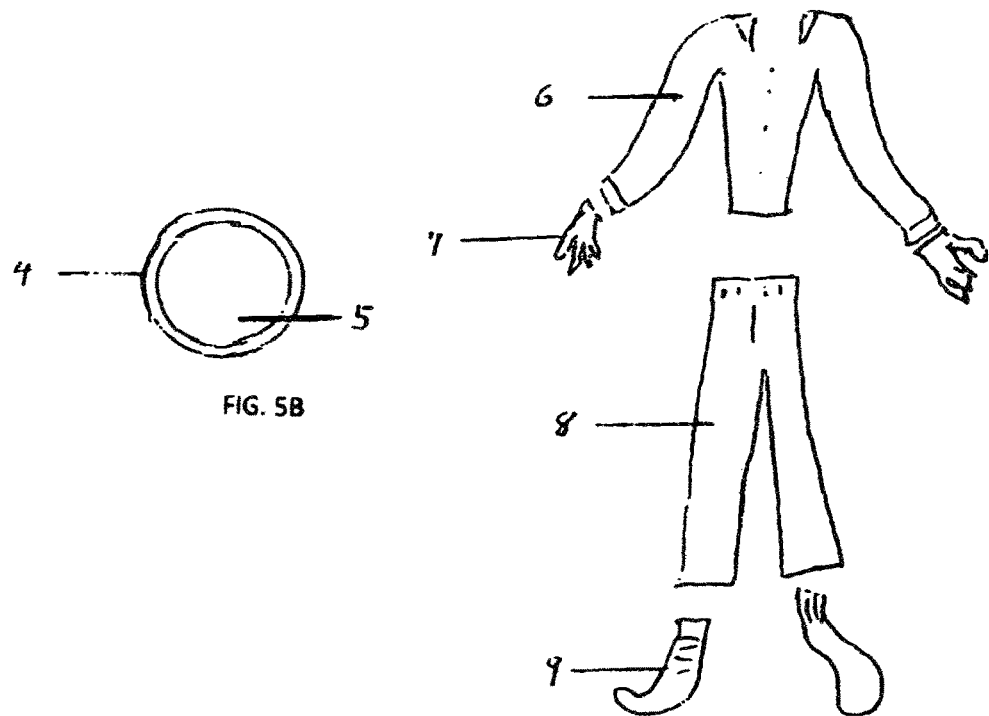
FIG. 5B
FIG. 5C

FIG. 8
TEST RESULTS

| Patient | Muscle | Placement | Disc | Muscle Strength |
|---|---|---|---|---|
| 1 | R. Anterior Leg Flexor | Umbilicus | Red | + |
| 2 | Right Hamstring | L-5 | Red | + |
| 3 | Left Supraspinatus | Umbilicus | Gold | + |
| 4 | Right Hamstring | L-5 | Red | + |
| 5 | Right Hamstring | L-5 | Red | + |
| 6 | Right Supraspinatus | Right Supraspinatus | Gold | - |
| 7 | Left Supraspinatus | Left Supraspinatus | Red | + |
| 8 | Left Hamstring | L-5 | Gold | - |
| 9 | Right Quadriceps | Umbilicus | Red | + |
| 10 | Left Supraspinatus | Left Supraspinatus | Gold | - |
| 11 | Right Hamstring | L-5 | Red | + |
| 12 | Right Supraspinatus | Umbilicus | Red | + |
| 13 | Left Hamstring | L-5 | Gold | - |
| 14 | Right Supraspinatus | Right Supraspinatus | Red | + |
| 15 | Right Hamstring | L-5 | Gold | - |
| 16 | Left Supraspinatus | Left Supraspinatus | Gold | + |
| 17 | Left Hamstring | L-5 | Gold | - |
| 18 | Right Quadriceps | Umbilicus | Red | + |
| 19 | Right Psoas | Umbilicus | Red | + |
| 20 | Right Psoas | Umbilicus | Gold | + |
| 21 | Right Supraspinatus | Umbilicus | Gold | + |
| 22 | Right Supraspinatus | Umbilicus | Gold | + |
| 23 | Left Supraspinatus | Umbilicus | Gold | + |
| 24 | Left Supraspinatus | Left Supraspinatus | Red | + |
| 25 | Left Supraspinatus | Left Supraspinatus | Red | + |
| 26 | Left Quadriceps | Umbilicus | Red | + |
| 27 | Left Supraspinatus | Left Supraspinatus | Red | - |
| 28 | Right Supraspinatus | Right Supraspinatus | Red | + |
| 29 | Right Quadriceps | Solar Plexus | Gold | + |
| 30 | Right Hamstring | L-5 | Gold | + |
| 31 | R. Sterus-Clido-Mast. | Solar Plexus | Red | + |
| 32 | Left Hamstring | L-5 | Gold | - |
| 33 | Right Hamstring | L-5 | Gold | - |
| 34 | Left Hamstring | L-5 | Red | + |
| 35 | Right Supraspinatus | Right Supraspinatus | Red | + |
| 36 | Left Hamstring | L-5 | Red | + |
| 37 | Left Hamstring | L-5 | Gold | - |
| 38 | Right Hamstring | L-5 | Red | + |
| 39 | Right Quadriceps | Umbilicus | Red | - |
| 40 | Right Deltoid | Umbilicus | Red | + |
| 41 | Left Hamstring | L-5 | Red | + |
| 42 | Right Hamstring | L-5 | Red | + |
| 43 | Left Hamstring | L-5 | Red | + |
| 44 | Right Supraspinatus | Right Supraspinatus | Red | + |

Steve Cutney's Experimental Data (Example 4)

| Date | Baseline Lift #1 | Intervention Lift #2 | Baseline Lift #3 | Intervention Lift #4 | Code |
|---|---|---|---|---|---|
| 1: 4-2-01 | 4 | 5 | 3 | 4 | A |
| 2: 4-5-01 | 4 | 3 | 2 | 1 | B |
| 3: 4-9-01 | 4 | 3 | 3 | 2 | B |
| 4: 4-12-01 | 5 | 5 | 4 | 6 | A |
| 5: 4-19-01 | 2 | 4 | 2 | 3 | A |
| 6: 4-22-01 | 2 | 3 | 2 | 3 | A |
| 7: 4-25-01 | 1 | 2 | 3 | 4 | A |
| 8: 4-29-01 | 3 | 4 | 2 | 3 | A |
| 9: 5-3-01 | 5 | 4 | 4 | 2 | B |
| 10: 5-4-01 | 4 | 5 | 3 | 4 | A |
| 11: 5-8-01 | 1 | 2 | 1 | 3 | A |
| 12: 5-10-01 | 3 | 3 | 2 | 1 | B |
| 13: 5-18-01 | 2 | 3 | 2 | 3 | A |
| 14: 5-22-01 | 2 | 2 | 1 | 0 | B |
| 15: 5-23-01 | 1 | 3 | 2 | 2 | A |
| 16: 5-24-01 | 4 | 4 | 3 | 4 | A |
| 17: 5-25-01 | 4 | 3 | 2 | 2 | B |
| 18: 5-24-01 | 2 | 3 | 2 | 1 | B |
| 19: 5-24-01 | 2 | 1 | 1 | 1 | B |
| 20: 5-29-01 | 3 | 3 | 2 | 1 | B |

| Weight | Wo/ AA | W/ AA | Wo/ AA | W/ AA |
|---|---|---|---|---|
| 115 | 11 | 14 | 12 | 15 |
| 220 | 3 | 5 | 5 | 5 |
| 80 | 4 | 5 | 5 | 3 |
| 140 | 3 | 4 | 4 | 5 |
| 110 | 4 | 6 | 3 | 3 |
| 170 | 3 | 175 → 4 | 175 → 3 | 180 → 5 |
| 165 | 7 | 9 | 8 | 9 |
| 155 | 6 | 8 | 6 | 4 |
| 115 | 9 | 7 | 6 | 6 |
| 145 | 12 | 9 | 7 | 7 |
| 155 | 1 | 2 | 2 | 2 |
| 140 | 1 | 3 | 1 | 2 |
| 175 | 6 | 180 → 6 | 185 → 6 | 185 → 7 |
| 145 | 6 | 8 | 7 | 8 |
| 185 | 3 | 5 | 4 | 5 |
| 135 | 6 | 140 → 6 | 140 → 4 | 140 → 6 |
| 95 | 2 | 4 | 3 | 3 |
| 125 | 5 | 7 | 6 | 7 |
| 185 | 3 | 4 | 2 | 4 |
| 160 | 7 | 9 | 8 | 10 |
| 180 | 2 | 185 → 4 | 185 → 2 | 185 → 4 |
| 155 | 4 | 5 | 160 → 3 | 160 → 5 |
| 85 | 2 | 4 | 2 | 3 |
| 170 | 1 | 3 | 1 | 3 |
| 190 | 1 | 190 → 2 | 195 → 2 | 200 → 2 |
| 135 | 1 | 2 | 140 → 0 | 140 → 1 |
| 165 | 0 | 1 | 0 | 1 |
| 85 | 1 | 4 | 3 | 4 |
| 65 | 1 | 2 | 1 | 3 |
| 80 | 2 | 3 | 1 | 2 |
| 145 | 6 | 9 | 8 | 7 |
| 135 | 6 | 7 | 5 | 6 |
| 180 | 4 | 5 | 3 | 5 |
| 185 | 3 | 5 | 4 | 5 |
| 115 | 8 | 8 | 8 | 5 |
| 160 | 4 | 7 | 6 | 6 |
| 155 | 12 | 15 | 13 | 14 |
| 125 | 11 | 13 | 13 | 14 |
| 160 | 5 | 6 | 4 | 5 |
| 95 | 12 | 15 | 13 | 12 |
| 140 | 2 | 3 | 2 | 4 |
| 225 | 2 | 2 | 2 | 4 |
| 135 | 1 | 3 | 0 | 2 |
| 160 | 7 | 8 | 6 | 7 |
| 135 | 1 | 3 | 0 | 2 |
| 165 | 12 | 12 | 10 | 9 |
| 215 | 3 | 3 | 2 | 2 |
| 170 | 5 | 6 | 4 | 5 |
| 145 | 8 | 10 | 10 | 7 |
| 130 | 9 | 6 | 7 | 5 |

Comparison of Placebo and Active Principle Intervention Results

- 1 to 2 indicates placebo to Active Principle
- 2 to 3 indicates Active Principle to Placebo
- 3 to 4 indicates Placebo to Active Principle

METHOD FOR INCREASING MUSCLE STRENGTH

This application is a Continuation of application Ser. No. 13/987,482; which is a Continuation of application Ser. No. 10/302,527 filed Nov. 25, 2002, now U.S. Pat. No. 8,617,590; which is a Continuation in Part of application Ser. No. 09/243,753 filed Jan. 21, 1999, now abandoned.

FIELD OF INVENTION

The present invention relates to the ability of nutrients to increase muscle strength when held on the body by a holding device during the performance of physical activity. The utility is that by wearing such devices during athletic endeavors performance is enhanced.

PRIOR ART

All patent documents cited above involve the stimulation of reflex zones on the soles of the feet to correct posture. These reflex zones once stimulated send afferent signals to the central nervous system. The reflex arc is completed when efferent signals are sent to the muscles resulting in an increased muscle tone, which moves the bones back into alignment.

The cited patents claim the therapeutic effects of crystals (U.S. Pat. No. 6,148,822-6,024,093) micro crystals in a magnetic flux (U.S. Pat. No. 5,158,526) and filtering film with a determined transmission curve (Canadian pat. No. 1,328,734) that are incorporated into pedal devices to correct posture.

These references all involve the non-pharmaceutical stimulation of mechanoreceptors on the soles of the feet that reflectively cause muscles to react and cause the skeletal system to move back into alignment. This resulting improved muscle strength and endurance is claimed by Cron, et al in U.S. Pat. No. 6,148,822 (claim 20).

Such an increase in muscle strength was observed by George Goodhart D.C. in 1970 when a nutrient inside a subject's mouth was chewed. Goodhart would then observe a phenomenal increase in the strength of weak indicator muscle. (Interestingly, the lower jaw and the TMJ are highly innervated by proprioceptive fibers.) Goodhart must be credited with his observation of increased muscle tone through stimulation caused by nutrients.

Over the last thirty years, this ability of nutrients to make weak muscles stronger has been embraced by nutritionists, kinesiologists, chiropractors, and physical therapists in testing nutrients. A large proportion of these also utilize the topical placement of various nutrients to result in the clinical observations of weak muscles becoming stronger.

It is the object of this invention that this resulting increase in muscle tone, routinely observed by such professionals, can translate into improved athletic performance if these nutrients are held next to the body (worn) while conducting exercise. This is the utility of the invention. Various nutrient holding devices are utilized for this purpose. The active agents are held in such devices in a waterproof enclosure separated from the surface of the body only by the thin covering of said enclosure (up to 3 mm).

It is the contention of this inventor that the soles of the feet are not solely responsible for the body's enormous proprioceptive input, which is actually spread out over the surface of the body. This allows for multiple placement sites for reflex-zone stimulation.

This is an obvious advantage over prior art that is limited to a pedal device (Cron, et al) and therefore subject to inevitable wear and tear on the device.

The present invention is distinguished from prior art in that it uses nutrients as the active principle. It does not use magnets, microcrystals in a magnetic flux, flexible filtering film, or sulfur powder and crystals as a means to stimulate reflex zones.

BRIEF DESCRIPTION OF DRAWINGS

FIG. 1-8 The various types of holding devices that together with the active principle (nutrients, nutritional supplements, metabolites) that can be utilized in this invention are given for the purpose of illustration and without restriction.

FIG. 3A. This illustrates an AP view of a pedal device which may be a shoe, a pedal insert, or the base of a sandal. The dotted outline indicates the position of the active principle which is sandwiched between a fabric, leather material or some other appropriate material (1) that pedal inserts could be made of.

FIG. 5A This depicts a hollow spool of thread (3). In the magnified view (1) of the thread, the thread is shown to be hollow (2). The active principle may be incorporated into such a thread. Then the resulting fiber becomes a nutrient holding device that can hold the active principle. The fiber must be waterproof to protect the integrity of the active agent. Then, the fiber can be woven into various articles of clothing that would provide the envisioned therapeutic effect while being worn.

FIG. 5B. This illustrates a cross section of such a fiber, the waterproof housing (4) and the resulting compartment for the active principle (5).

FIG. 5C. This illustrates the various articles of clothing when such fibers are used in producing clothing. Specifically, a shirt (6), gloves (7), pants (8), and socks (9) are illustrated.

FIG. 8. This is a table showing the experimental results generated by Dr. Frio in Example 1.

FIG. 9. This is a table showing the experimental data generated by Steve Cutney in Example 4.

FIG. 10. This is a table showing the experimental data generated by Steve Cutney in Example 7.

SUMMARY OF THE INVENTION

Figure 1A:
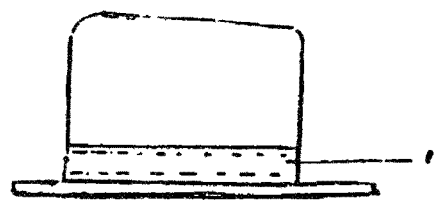
FIG. 1A This illustrates a hat. The nutrient holding device is incorporated in a band (1) that goes around the circumference of the hat holding the active principle next to the skull.

The invention relates to a method, which comprises a nutrient holding device, which contains a compartment, which houses nutrients. These active agents (nutrients, metabolites) can stimulate reflex zones located on the surface of the body (head, neck, back, foot, pelvis, umbilicus, chest, feet solar plexus etc.). It is believed that these agents deliver natural frequencies and radiations, which affect these reflex zones. Therefore, by placement of said device on the surface at various locations on the body the utility of the invention can be realized. The nutrient holding device secures the active agents on the body surface during athletic endeavors.

The invention therefore comprises a nutrient holding device, such as a locket, belt, pedal device, necklace, shoe, (or it may be incorporated into clothing). This device contains one or several types of selected nutrients such as vitamins, minerals amino acids, phytomorphagens, herbs, enzymes and hormones. All of these substances are metabolites, and are themselves or constituents of them found naturally occurring in life forms. They may be in a powder, liquid, or gel form. They are encased in the holding device in waterproof housing. The holding device secures these active agents on the surface of the body on a variety of locations throughout the surface of the body where mechanoreceptors can be stimulated. As will be explained below, mechanoreceptors are the most abundant receptors on the surface of the body. This allows for the multiple placement of the nutrient holding devices.

Those parts of the body that receive stimuli at the termination of peripheral afferent fibers are known as receptors. The human body is receptors driven. Eighty percent of neurology is afferent, only 20% efferent. Of this eighty percent, 80% are mechanoreceptors (involved in posture and protecting the central nervous system).

The most abundant type of sensory endings in the body are non-encapsulated afferent endings found in practically all epithelia of the body, in connective tissue and in serious membranes. Therefore, although the feet are important sites of mechanoreceptor, they are by no means solely responsible for the enormous proprioceptive input from the entire surface of the body. Hence, in addition to the feet other placement sites on the body may be used to stimulate these receptors.

The method of placing these active agents in a holding device that secures the nutrient on the body has the effect of stimulating the mechanoreceptors, which send out impulses to the central nervous system. This is the first part of the reflex arc.

The reflex arc is completed by the central nervous system sending efferent nerve impulses to the muscles. The result is an increase in muscle tone that can be measured in the ability to lift a specific weight more times. Since the muscle tone and strength are increased, this method of wearing this stimulus-producing agent using the nutrient holding devices during athletic endeavors has an apparent utility.

The active principle of the nutrient holding device may be a combination of one or several nutrients or food supplements. Both the type and amount of nutrients to be used alone or in combination are selected based on their ability to stimulate the mechanoreceptors located throughout the surface of the body, and thereby cause a reflex back to the muscles increasing strength and endurance. Indeed, all nutrients have the potential ability to stimulate these reflex zones.

The nutrients may be selected from the following groups that are listed as illustrative examples:

Herbs/phytonutrients—grape seed extract, garlic, flax seed oil, *ginseng*, ginger *Echinacea, chlorella*, bromelain, beet root, algae, bee pollen etc.

Amino Acids—L-acetyl glucosamine, L-taurine, L-valine, inosine, GABA, creatine monohyrate, L-alanine, L-carnosine etc.

Enzymes—amylase, betaine, lipase, pancreatin, pepsin, trypsin.

Vitamins—Vitamin A, Beta Caratine, Vitamin C, Vitamin D, Vitamin E, Niacin, Biotin, Inositol, PABA, Vitamin B12, Vitamin B6, Vitamin B5, Vitamin B1, Vitamin B2, Folic Acid.

Glandular, phytomorphagens, DHA, EPA, Coenzyme Q-10 Chrondrotin Sulfate, Chitin, Bovine Cartilage.

Hormones DHEA, Melatonin, Pregnenolone, DMAE, CMO, NADH, HGH

Minerals in the form of metabolites

Essential fatty acids

PREFERED EMBODIMENTS 1. 3 tablespoons of blue-green algae
2. 1 tablespoon of blue-green algae
    tablespoon of Immuno-forte (a mixture of glandulars from Douglas Laboratories)
    1 tablespoon of Ultrapreventive III ( multi-vitamin-mineral formula from Douglas Laboratories)
3. 3 tablespoons of Ultrapreventive III powder (Douglas Laboraories)
4. 3 grams of 1000-k Alternative Formula (a prescription formula)
    1 gram of DHEA
    1 gram of Pregnenolone
    50,000 units of Beta Carotene -continued

PREFERED EMBODIMENTS

Ultra B-Complex (4) tablets
    Natural C 500 (4) tablets
    100 mg of Pyenogenol
    units of Multi-E-400, Natural Dry
    3 grams of Free Form Amino Caps
    1 gram of Max-Taurine
    1 gram of L-Lysine
    1 gram of Creatine Monohydrate
    2 grams of Ora-Multi (blend of 9 glandulars) (Douglas Laboratories)
5. 500 mg of Balanced-B complex
    20 grams of Goldenseal Root Powder
    200 mg of Ginkgo Biloba
    1 gram of Echinacea
    8 capsules of Herbplex
    Vitamin D Formula 3,000 IU
    Multi-E-200 (4) Capsules
    3 grams of Chlorella Plus
    6 capsules of Immuno-forte
    (the above formulations are from Douglas Laboratories)
6. 2 teaspoons of Ulltrapreventive III Powder (Douglas Laboratories)
    1 teaspoon of Ultragreen powder (Douglas Laboratories)
    3 grams of Ori-Multi a blend of glandular (Douglas Laboratories)
    4 capsules of HerbPlex (Douglas Laboratories)
    4 capsules of Aminoplus
    1 teaspoon of Bee Pollen Granules
    3 capsules of Ultimate Balance (prescription formula 47)
    Shark Cartilage - 400 mg (Burn Stone Labs)
    Octaconsonal - 1000 mcg (Burn Stone Labs)
    Chromium Picolonate 200 mcg (Burn Stone Labs)
7. 1 tablespoon of Ultrapreventive III
    3 grams of Ori-multi (a glandular extract)
    3 grams of Immuno-forte
    3 grams of Blue-Green Algae
    300 mg DHEA
    200 mg Pregnelone
    5 grams of Amino Plus

EXAMPLES

The instant invention will become more understood by referring to the following examples, which is given to picture more readily the invention rather than limit its scope.

Example I

This experiment is an example of how preferred embodiment #1 can be used at multiple locations with success in making weak muscles stronger. The following locations are used: the umbilicus, the left and right upper back, the lower back (L-5) and the solar plexus.

The preferred embodiment being exemplified here is three tablespoons of blue green algae powder encased in a plastic coated disk three inches in diameter and 0.25 inches thick.

Dr. Dominic Frio is a chiropractor that has practiced in New Jersey for 25 years and a U.S citizen for 50 years.

He was given two disks to evaluate using manual muscle testing. The disks were all of the same size, shape, and weight. They were color-coded gold and red. He was not told which was the placebo and which was the active agent. An assistant put each disk into separate envelopes.

His evaluation consisted of locating a weak muscle, which was recorded (see recorded data in appendix). His assistant presented the two identical envelopes to him from outside the examination room. Then he would ask his patient to pick one of the envelopes. He would then place the envelope on the body at various locations, which were noted.

He then retested the muscle to determine if it had weakened or strengthened. This data was than recorded.

The color of the disk was only logged after taking it out of the envelope. The disk was given back to his assistant, who put it in the envelope for the next trial. Forty-four patients were used in this study.

Thus a control group consisting of 16 subjects was generated and provided these results:
    10 muscles remained weak
    6 muscles tested stronger A separate group that used the intervention of the nutritional supplement was generated and produced these results:
    2 muscles remained weak
    26 tested stronger Conclusion: Overall the placement of this disk containing blue-green algae at multiple locations has proven effective in making weak muscles stronger. If it is worn during exercise, as in the next example, performance is enhanced.

Example II

The following study is provided as an example of the utility of the invention:

The nutrient used in this study is three tablespoons of blue-green algae encased in a plastic disk 3 inches in diameter and 0.25 inches thick.

This is an example of how to make and use the invention. Simply, wear the nutrient holding device and exercise. In this case, placement of the disk on the chest is exemplified. This holding device holds the active agent flush to the chest of the subject separated from the body only by the thin housing of the device.

One student was tested on a bench press. Prior to testing, he had warmed up and stretched. The first lift was done to establish a baseline. The amount of weight was his estimated one repetition maximum. There was no intervention of an active agent or placebo in this first exercise. In this first exercise, he was instructed to lift this weight as many times as he could through a full range of motion until muscle failure or fatigue. Five minutes later he drew a color-coded locket encased in a sock from a black bag containing a placebo locket and an active agent locket. The locket encased in the sock was placed on the subject's chest. He was then instructed to lift the weight as many times as he could until muscle failure. The results were recorded. The color of the locket was revealed from the sock. These results were also recorded. The weights were reduced as the subject's ability decreased over time. The amount of weight lifted was logged.

The above procedure was repeated every five minutes. The following data was collected:

| Weight | Baseline | S/I | Color |
| --- | --- | --- | --- |
| 160 lbs. | 1 repetition | 0 | Gold |
| 160 lbs. | 0 repetition | 1 | Red |
| 155 lbs. | 3 repetitions | 2 | Gold |
| 155 lbs. | 2 repetitions | 3 | Red |
| 145 lbs. | 2 repetitions | 1 | Gold |
| 135 lbs. | 2 repetitions | 2 | Gold |
| 135 lbs. | 2 repetitions | 3 | Red |
| 125 lbs. | 3 repetitions | 4 | Red |
| 125 lbs. | 2 repetitions | 3 | Red |

Conclusion

Overall, the subject performed with increased ability when wearing the Red locket (active agent) as compared to the Gold locket (placebo).

Example III

This small study is a controlled; double blind study done by an independent investigator, Renece Garcia, D.C. in Shreveport, La.

This is an example of placement of the active principle on the umbilicus. The preferred embodiments being exemplified are three tablespoons of Ultra Preventative III powder encased in the buckle of a support belt that was sent to her with an identical placebo (see appendix for ingredients of Ultra Preventative III Powder).

The active principle was hidden in a belt buckle and marked "A" on the underside. This mark was covered by tape. The other belt likewise was marked "PL" on the underside of the belt buckle and was covered by identical tape.

The first subject was analyzed for strength of the psoas muscles. A leg measurement was conducted. The results were logged.

Next, the subject drew one of the identical belts out of a black bag. The subject put the belt on. The psoas muscles were tested again and the leg lengths were measured again. Any changes in the strength of the psoas and leg lengths were noted. The subject then put the remaining belt on. The psoas muscles were tested and leg lengths were measured. The results were noted.

The tape was then removed from the second belt, and the belt was identified and logged. The other belt's identity was also logged.

Seven patients were put through the same regime, generating a placebo group and an identical group testing the active agent.

Although the subjects were used as their own controls, the method of randomly drawing the belts after testing parameters preserves the integrity of this randomized double blind study.

The results were as follows:
Clinical Findings

CLINICAL FINDINGS

| No. | Preliminary Findings | Control | Intervention of Active Agent |
|---|---|---|---|
| 1 | 21 year-old W/F | | |
| | Short left leg | No change | Equalized leg length |
| | Weak left psoas | No change | Strong left psoas |
| 2 | 20 year-old W/F | | |
| | Even leg lengths | — | — |
| | Weak right psoas | No change | Strong left psoas |
| 3 | 52 year-old W/F | | |
| | Even leg lengths | No change | No change |
| | Weak right psoas | No change | No change |
| 4 | 43 year-old W/F | | |
| | Short right leg | No change | Equalized leg length |
| | Weak right psoas | No change | No change |
| 5 | 57 year-old W/F | | |
| | Short right leg | No change | Equalized leg length |
| | Weak right psoas | No change | No change |
| 6 | 49 year-old W/M | | |
| | Even leg lengths | — | — |
| | Weak right psoas | No change | No change |
| 7 | 43 year-old W/M | | |
| | Short right leg | No change | Equalized leg length |
| | Weak right psoas | No change | Strong right psoas |

Results:
No change in leg length and psoas muscle strength was noted in the control group. The active agent intervention showed two patients with no change of leg length or psoas strength.

Four subjects, each of whom had a short leg in preliminary measurements, had equal leg lengths with the intervention of the active agent.

Note: Two subjects had even leg lengths in the preliminary measurement, therefore a (--) in the chart indicates no comparison was made.

Four of the seven subjects showed an increase in psoas strength, while three subjects' psoas strength measurements remained weak.

Discussion:

The control group did not show any change in either leg length or psoas muscle strength.

The group with the active agent intervention showed changes in leg length and/or muscle strength in five patients.

This change can only be due to the intervention of the active agent.

The significance of an increase in muscle strength is obvious. The significance of leg length equalization can only be due to an increase in muscle tone resulting in movement of the pelvis, thus equalizing leg length.

The utility of the invention using this preferred embodiment #3 is practiced in the following example where the subjects conduct an exercise regimen while wearing this embodiment.

Example IV

The following study is an example of utilizing preferred embodiment #3. (see appendix for exact formula) which has been incorporated into a medallion or locket (FIGS. IIA&B). The utility of this locket is realized during the following exercise regimen as it is compared to the performance of a placebo group.

Therefore, to examine how the use of this device results in increased strength and endurance, Steven J. Cutney, the strength and conditioning coach of Mt. Vernon High School performed the following placebo controlled double blind study.

He was given two identical medallions. They had the same size, shape, weight, and color. He was not told which was the placebo and which was the active agent. The medallions were coded for differentiation.

Twenty subjects were tested on a bench press using four separate lifts. Prior to testing, all athletes were provided with a warm-up and stretching session of uniform intensity and duration. The time between each lift was about five minutes. All subjects were given standardized instructions "Press the weight as many times as you can until muscle fatigue or muscle failure.

All subjects lifted 90 percent of their IRM (one repetition maximum). The first lift is done to establish a baseline and is done without having a medallion on the body. The objective results were recorded as whole numbers, indicating the number of repetitions completed through a full range of motion. The subject then draws a medallion that has been encased in an envelope out of a black bag. The bag has both medallions encased in separate envelopes.

Before starting the second lift, he places the envelope on the solar plexus of the subject. The instructions were repeated to the subject, and he completed his maximum effort. The results were then recorded (see accompanying chart).

The third lift was done to establish a second baseline and is done without having a medallion on the body. The instructions were repeated and the subject completed his maximum effort. The results were then recorded.

The fourth lift was done with the same envelope on the subject's solar plexus. The instructions were repeated and the subject completed his maximum effort. The results were then recorded.

Upon completion of the lifts, the envelope was opened and the code was recorded. The medallion was put into a new envelope and returned to the black bag for subsequent tests.

The data was given to this investor for interpretation (see appendix for data chart)

Conclusion

The subjects were able to perform their prescribed exercises with increased ability due to the intervention of the active agent A as compared to placebo intervention B.

Example V

Figure 1B:
FIG. 1B. This is a longitudinal cross-section of the band showing the waterproof housing (2) which makes up the compartment holding the active principle (3).
Figure 2A:
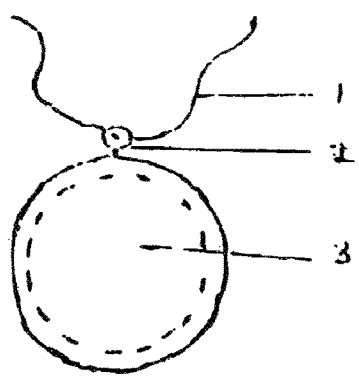
FIG. 2A. This pictures the holding device as a locket or disc. This AP view shows the outer plastic covering of the device (3), a clasp (2), and chain (1) which allows the device to hang around the neck of the subject at locations on the chest or solar plexus. The diameter of the locket is 3 inches and the width is 0.25 inches.
Figure 2B:
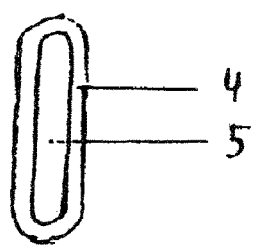
FIG. 2B. This pictures a cross sectional view of the locket illustrating the plastic membrane (4) around the device and the resulting waterproof compartment containing the active principle (5).
Figure 3A:
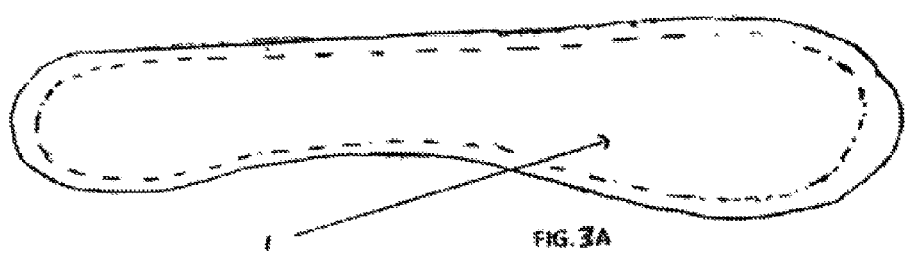
Figure 3B:
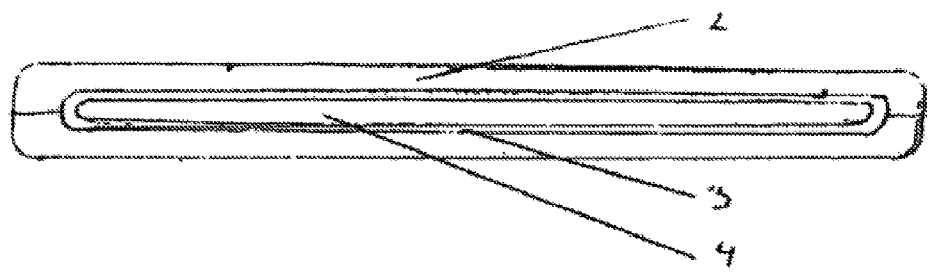
FIG. 3B. This illustrates a longitudinal cross section of this pedal device. The outer covering (2) of the device may be composed of leather, plastic, foam or gel or rubber that surrounds a waterproof housing (3) which contains the active principle (4).
Figure 4A:
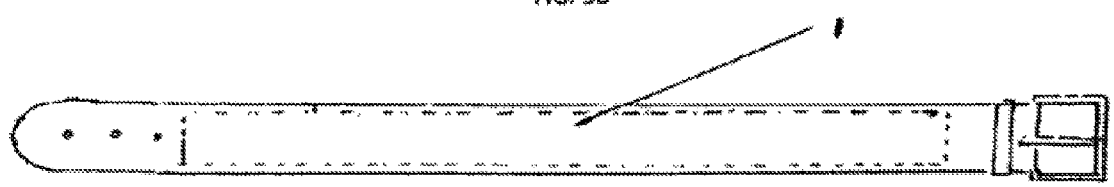
FIG. 4A. This pictures the holding device as a belt. This AP view shows the outer covering (1) of the belt which is preferably leather, but may be plastic or other material. The dotted line indicates the location of the active principle which would be held next to the waist in this particular device.
Figure 4B:
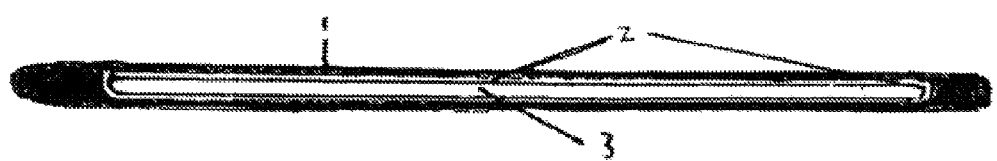
FIG. 4B. This is a longitudinal cross section of the belt illustrating the outer covering (1) that surrounds a waterproof compartment that may be in the form of a plastic insert (2) which surrounds the active principle (3).
Figures 6A, 6B, 7A, 7B:
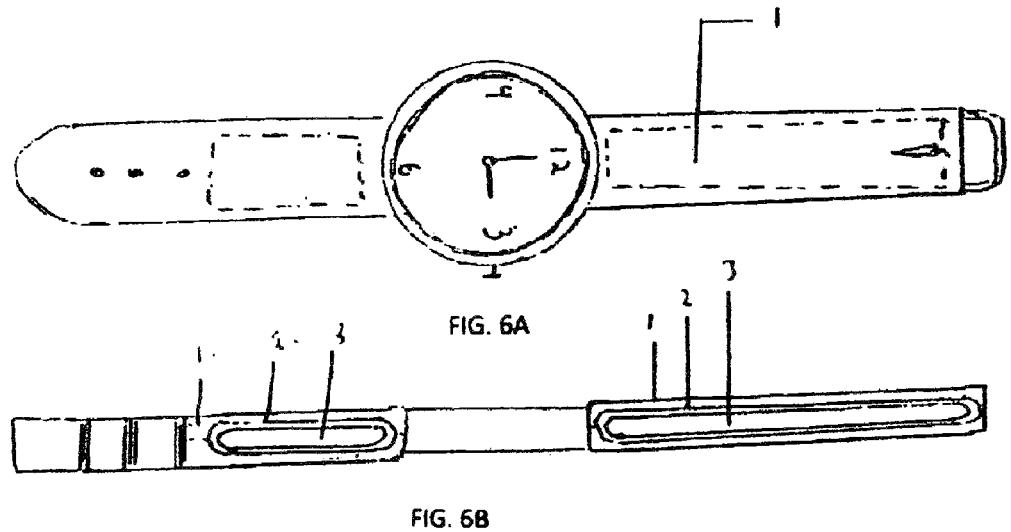
FIG. 6A. This illustrates a watchband as a holding device. The active principle (1) is sandwiched between two pieces of leather which make up the watchband.
FIG. 6B. This illustrates a cross section of the watchband. The leather material (1) surrounds a waterproof plastic insert (2) which contains the active principle (3).
FIG. 7A This pictures an AP view of a ring that can act as a holding device. It may be composed of a metal (1) such as gold, silver, platinum, copper, etc.
FIG. 7B. As seen in this cross sectional view, the hollow chamber (2) of the ring can act as a holding device for the active principle thus providing the envisioned therapeutic response while being worn.
Figure 11:
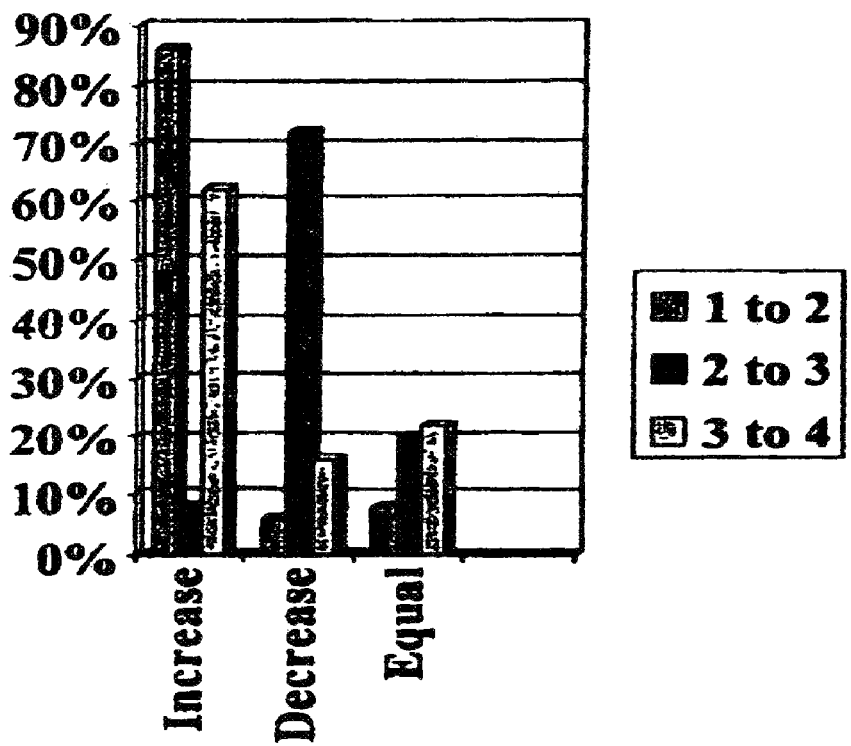
FIG. 11. This is a comparison chart of the results in the experiment by Steve Cutney in Example 7.
Figure 12:
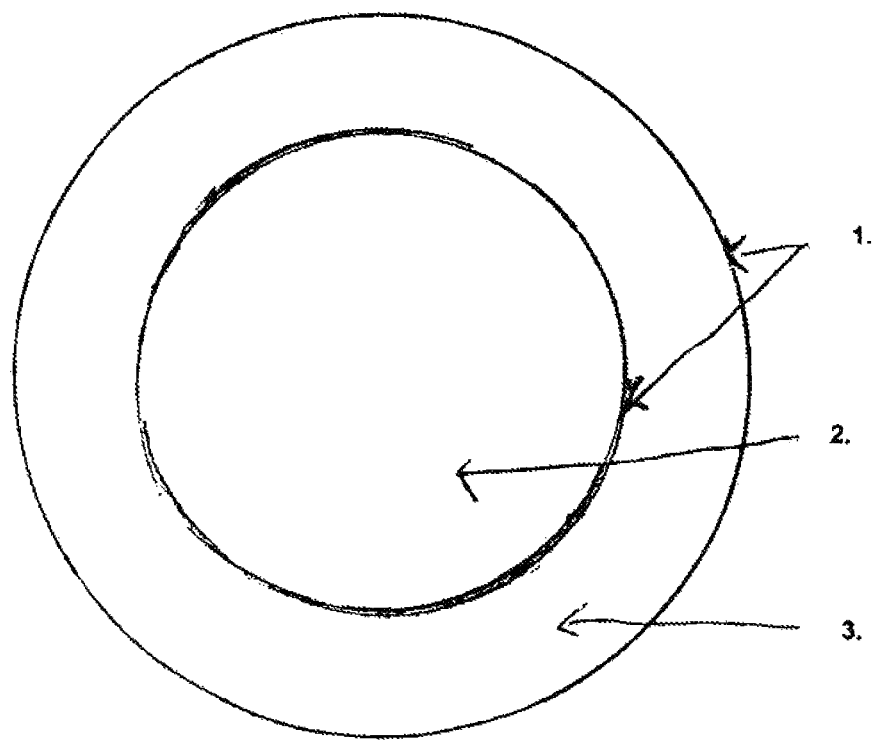
FIG. 12A. This illustrates the nutrient holding device as a non transdermal patch. In this AP view the plastic covering (1) forms a compartment (2) containing the nutrient material. The patch is held on various locations on the body with a medical adhesive (3).
FIG. 12B. This illustrates a cross sectional view of the non transdermal patch. The plastic lining (1) forms a waterproof compartment (2) containing the nutrient material. A medical adhesive (3) is used to secure the patch to the skin.
Figure 12:
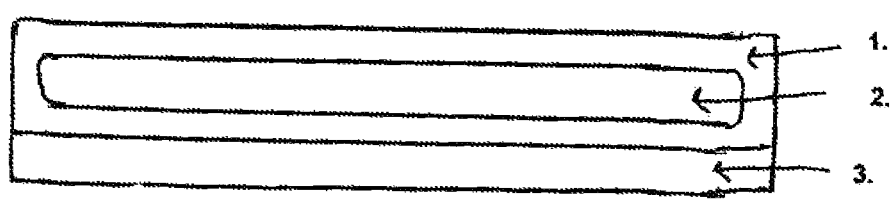

The ability of preferred embodiment #4 when employed in the band of a hat (FIG. 1) to improve the strength of a weak muscle was confirmed by repeated observations of over 50 separate and distinct instances. These subjects were screened as to the presence of a weak supraspinatus. Then they were asked to put the hat on allowing placement of the active agent to be around the circumference of the skull. Using manual muscle testing the superaspinatus was retested and found to have increased muscle tone in the vast majority of instances. Therefore, this placement of the active agent may be utilized to practice the invention such as a hat or helmet is worn during athletic endeavors.

Example VI

Preferred embodiment #5 was used in a pedal device (FIG. IIIA). The active principle was encased in the waterproof housing (FIG. IIIB,3). Twenty subjects were screened and found to have a weak anterior leg flexor. The subjects would then slip into the above sandals and be retested with the vast majority showing improvement in muscle tone. Therefore, this placement of the active agent may be utilized to practice the invention by wearing such a pedal device (i.e. sneaker) when performing athletic endeavors.

Example VII

Preferred embodiment #7 was utilized in the construction of a locket (FIG. IIB). This active agent (5) is occupying the waterproof compartment created by the plastic covering of this holding device.

An identical locket was constructed of the same size, shape, and weight to act as a placebo.

The lockets were color-coded and the identity of the placebo and active agent were revealed to Steve Cutney, strength and conditioning coach of Mount Vernon High School.

He conducted the following single blind study to compare the performance of 50 naïve athletes ages 16 to 18 when performing an exercise regimen using the placebo and active agent.

Testing was done on a bench press, which is highly reliable and valid for testing upper body strength.

All subjects were provided a warm-up of uniform intensity and duration prior to testing.

All subjects were given standardized instructions "Press the weight as many times as you can until muscle fatigue or muscle failure.

Four separate lifts were done. The time between each lift was about 5 minutes.

The first lift was done with the placebo; the second lift was done with the active agent, the third with the placebo and the fourth with the active agent.

A comparison was made on the performance of each athlete between the first placebo lift and second active agent lift, the second active agent lift and the third placebo lift and finally the third placebo lift and the forth active agent lift. It was noted whether there was an increase or decrease in the number of repetitions between each set.

The results are summarized as follows:
From Lift 1 (Placebo) to Lift 2 (Active Agent):
  86% lifted the weight more times using the active agent as compared to the placebo.
  6% lifted the weight fewer times with the active agent as compared to the placebo.
  8% remained the same
Comparison of Lift 2 to Lift 3
  8% had more repetitions with the placebo
  72% had fewer repetitions with the placebo
  20% had no change in repetitions
Comparison of Lift 3 to Lift 4
  62% had more repetitions with the active agent
  16% had fewer repetitions with the active agent
  22% had no change in repetitions

What is claimed is:

1. A nutrient holding apparatus for holding a nutrient near the skin of a wearer to provide a beneficial biological effect, wherein the apparatus comprises:
   a patch, wherein the patch comprises:
     an adhesive surface;
     a sealed enclosure for containing a nutrient, wherein the sealed enclosure comprises a waterproof housing; wherein the sealed enclosure does not allow transfer of the nutrient to the skin of the wearer; and
     a nutrient;
   wherein the adhesive surface faces away from the center of the sealed enclosure;
   further wherein the adhesive surface is operable to attach the sealed enclosure to the skin of a wearer;
   wherein the nutrient is comprised of an amino acid.

2. The nutrient holding apparatus of claim 1, wherein the amino acid is comprised of Carnitine.

3. The nutrient holding apparatus of claim 1, wherein the amino acid is comprised of L-Carnitine.

4. The nutrient holding apparatus of claim 1, wherein the amino acid is comprised of acetyl-L-Carnitine.

5. The nutrient holding apparatus of claim 1, wherein the amino acid is comprised of Arginine.

6. The nutrient holding apparatus of claim 1, wherein the amino acid is comprised of Gluthamic acid.

7. The nutrient holding apparatus of claim 1, wherein the amino acid is comprised of Glycine.

8. The nutrient holding apparatus of claim 1, wherein the amino acid is comprised of Leucine.

9. The nutrient holding apparatus of claim 1, wherein the amino acid is comprised of Isoleucine.

10. The nutrient holding apparatus of claim 1, wherein the amino acid is comprised of Valine.

11. The nutrient holding apparatus of claim 1, wherein the amino acid is comprised of Methionine.

12. The nutrient holding apparatus of claim 1, wherein the amino acid is comprised of Taurine.

13. The nutrient holding apparatus of claim 1, wherein the amino acid is comprised of Carnosine.

14. A nutrient holding apparatus for holding a nutrient near the skin of a wearer to provide a beneficial biological effect selected from the group of beneficial biological effects comprising: pain relief, increased energy, increased endurance, and an improved sense of well-being, wherein the apparatus comprises:
- an adhesive surface;
- a sealed enclosure for containing a nutrient, wherein the sealed enclosure comprises a waterproof housing; wherein the sealed enclosure does not allow transfer of the nutrient to the skin of the wearer; and
- a nutrient;

wherein the adhesive surface faces away from the center of the sealed enclosure;

further wherein the adhesive surface is operable to attach the sealed enclosure to the skin of a wearer;

further wherein the nutrient comprises an amino acid.

15. The nutrient holding apparatus of claim 14, wherein the amino acid is comprised of Carnitine.

16. The nutrient holding apparatus of claim 14, wherein the amino acid is comprised of L-Carnitine.

17. The nutrient holding apparatus of claim 14, wherein the amino acid is comprised of acetyl-L-Carnitine.

18. The nutrient holding apparatus of claim 14, wherein the amino acid is comprised of Arginine.

19. The nutrient holding apparatus of claim 14, wherein the amino acid is comprised of Gluthamic acid.

20. The nutrient holding apparatus of claim 14, wherein the amino acid is comprised of Glycine.

21. The nutrient holding apparatus of claim 14, wherein the amino acid is comprised of Leucine.

22. The nutrient holding apparatus of claim 14, wherein the amino acid is comprised of Isoleucine.

23. The nutrient holding apparatus of claim 14, wherein the amino acid is comprised of Valine.

24. The nutrient holding apparatus of claim 14, wherein the amino acid is comprised of Methionine.

25. The nutrient holding apparatus of claim 14, wherein the amino acid is comprised of Taurine.

26. The nutrient holding apparatus of claim 14, wherein the amino acid is comprised of Carnosine.

* * * * *